US010751070B2

(12) United States Patent
Pendleton et al.

(10) Patent No.: US 10,751,070 B2
(45) Date of Patent: Aug. 25, 2020

(54) FEMORAL HIP STEM EXPLANT SYSTEM AND METHODS OF USING THE SAME

(71) Applicant: Tightline Development, LLC, Atlanta, GA (US)

(72) Inventors: John E Pendleton, Atlanta, GA (US); Daniel H Hursh, Roswell, GA (US); Thomas L Bradbury, Atlanta, GA (US)

(73) Assignee: SHENZHEN RIDER THINKING TECHNOLOGIES CO., LTD., Shenzhen (CN)

( * ) Notice: Subject to any disclaimer, the term of this patent is extended or adjusted under 35 U.S.C. 154(b) by 356 days.

(21) Appl. No.: 15/877,319

(22) Filed: Jan. 22, 2018

(65) Prior Publication Data

US 2018/0206859 A1    Jul. 26, 2018

Related U.S. Application Data

(60) Provisional application No. 62/450,112, filed on Jan. 25, 2017.

(51) Int. Cl.
*A61B 17/16* (2006.01)
*A61F 2/46* (2006.01)
*A61B 17/17* (2006.01)

(52) U.S. Cl.
CPC ...... *A61B 17/1668* (2013.01); *A61B 17/1604* (2013.01); *A61B 17/1637* (2013.01); *A61F 2/4607* (2013.01); *A61B 17/1742* (2013.01); *A61F 2002/4619* (2013.01); *A61F 2002/4681* (2013.01)

(58) Field of Classification Search
CPC ............ A61B 17/1604; A61B 17/1659; A61B 17/1668; A61B 17/1742; A61B 17/175; A61B 17/142
See application file for complete search history.

(56) References Cited

U.S. PATENT DOCUMENTS

| 3,815,599 A | * | 6/1974 | Deyerle | ............. | A61B 17/1659 |
|  |  |  |  |  | 606/85 |
| 5,591,170 A | * | 1/1997 | Spievack | ............. | A61B 17/151 |
|  |  |  |  |  | 30/122 |
| 7,998,146 B2 |  | 8/2011 | Anderson |  |  |

(Continued)

OTHER PUBLICATIONS

Publication titled "Flexible Osteotome System", Copyright 2015 Innomed, Inc. (one page).

(Continued)

*Primary Examiner* — Olivia C Chang
(74) *Attorney, Agent, or Firm* — FisherBroyles LLP; Anthony Dovale; John Boyd

(57) ABSTRACT

A system for facilitating the removal of a prosthetic hip implant from a femur. The explant system has at least one blade coupled to a handle. The shape of the blade conforms to a portion of the implant so that a cutting tip of the blade can be positioned in a desired position relative to the implant and the femur. A plurality of blades can be provided, each blade configured to conform to a different portion of the implant. Force is applied to the handle so that the cutting tip of the blade cuts through bone growth from the femur into the implant, thereby facilitating removal of the implant.

25 Claims, 19 Drawing Sheets

(56) References Cited

U.S. PATENT DOCUMENTS

2013/0226189 A1* 8/2013 Young .................. A61F 2/4607
606/99

OTHER PUBLICATIONS

Publication titled "Whelan Curved Chisel Guide", Copyright 2016 Innomed, Inc. (one page).
Publication titled "Whelan Flexible Chisel Guide", Copyright 2014 Innomed, Inc. (one page).

* cited by examiner

FEMORAL HIP STEM EXPLANT SYSTEM AND METHODS OF USING THE SAME

RELATED APPLICATIONS

This application claims the benefit of and priority to U.S. Provisional Application No. 62/450,112, entitled "FEMORAL HIP STEM EXPLANT SYSTEM", filed Jan. 25, 2017, which is hereby incorporated by reference in its entirety.

FIELD OF THE INVENTION

The present invention relates generally to systems and methods for the removal of hip implants. More specifically, the present invention relates to a system comprising a Femoral Hip Stem Explant assembly that facilitates the removal of a prosthetic implant from the femur and methods of using the same.

BACKGROUND OF THE INVENTION

Conventional, primary total hip replacement is a durable operation in the majority of patients. A hip replacement is a mechanical device with parts, comprising a ball and socket. As with any other mechanical device, a total hip replacement can be subject to various forms of mechanical or biological failure. Such a failure may require a reoperation of the hip replacement to address the cause of failure and its consequences. A reoperation of a total hip replacement is called a revision.

The parts of a hip replacement which move against one another will slowly wear down during the regular use of the replacement. The younger and the more physically active the patient is, the faster the wear. Continual, repetitive movement of the mechanical parts causes small pieces of hip prosthesis to break off. Depending on the type of hip replacement, these particles can be made out of plastic, cement, ceramic, or metal.

Mechanical wear and tear leading to loosening of the prosthesis (implant) is one of the most frequent forms of mechanical failure. However, other forms of mechanical failure are possible, like breakage of the prosthesis, such as may occur during a trauma like a fall or auto collision.

During revision surgery it can be difficult to remove the broken and remaining parts of the implant. Accordingly, it is desirable to provide a system that can assist the surgeon in removing the implant in an efficient manner with the least amount of damage to the bone and surrounding tissue.

SUMMARY

Presented herein is a system for the removal of hip implants and method of using the same. More specifically, a Femoral Hip Stem Explant system that facilitates the removal of a prosthetic implant from the femur is provided. In one aspect, the explant system comprises at least one blade coupled to a handle. A user, such as a surgeon and the like, can use the handle to guide the blade to a desired position relative to the implant and the femur. Force can then be applied to the handle so that a cutting tip of the blade cuts through bone growth from the femur into the implant, thereby facilitating removal of the implant.

In one aspect, the at least one blade of the explant system comprises a plurality of blades. In this aspect, each blade can be configured to conform to a portion of the implant. For example, the system can comprise at least a first blade configured to conform to the anterior and posterior portions of the implant, a second blade configured to conform to the lateral portion of the implant and a third blade configured to conform to the medial portion of the implant. In use, for example, the user can use the first blade to cut through bone growth from the femur into the anterior and the posterior portions of the implant, the second blade to cut through bone growth from the femur into the lateral portions of the implant, and the third blade to cut through bone growth from the femur into the medial portions of the implant.

Related methods of using and/or operation are also provided. Other apparatuses, methods, systems, features, and advantages of the devices and systems for explanting the femoral implant of a hip revision surgery will be or become apparent to one with skill in the art upon examination of the following figures and detailed description. It is intended that all such additional apparatuses, methods, systems, features, and advantages be included within this description, be within the scope of the devices and systems for explanting the femoral implant, and be protected by the accompanying claims.

DESCRIPTION OF THE INVENTION

Figure 1:
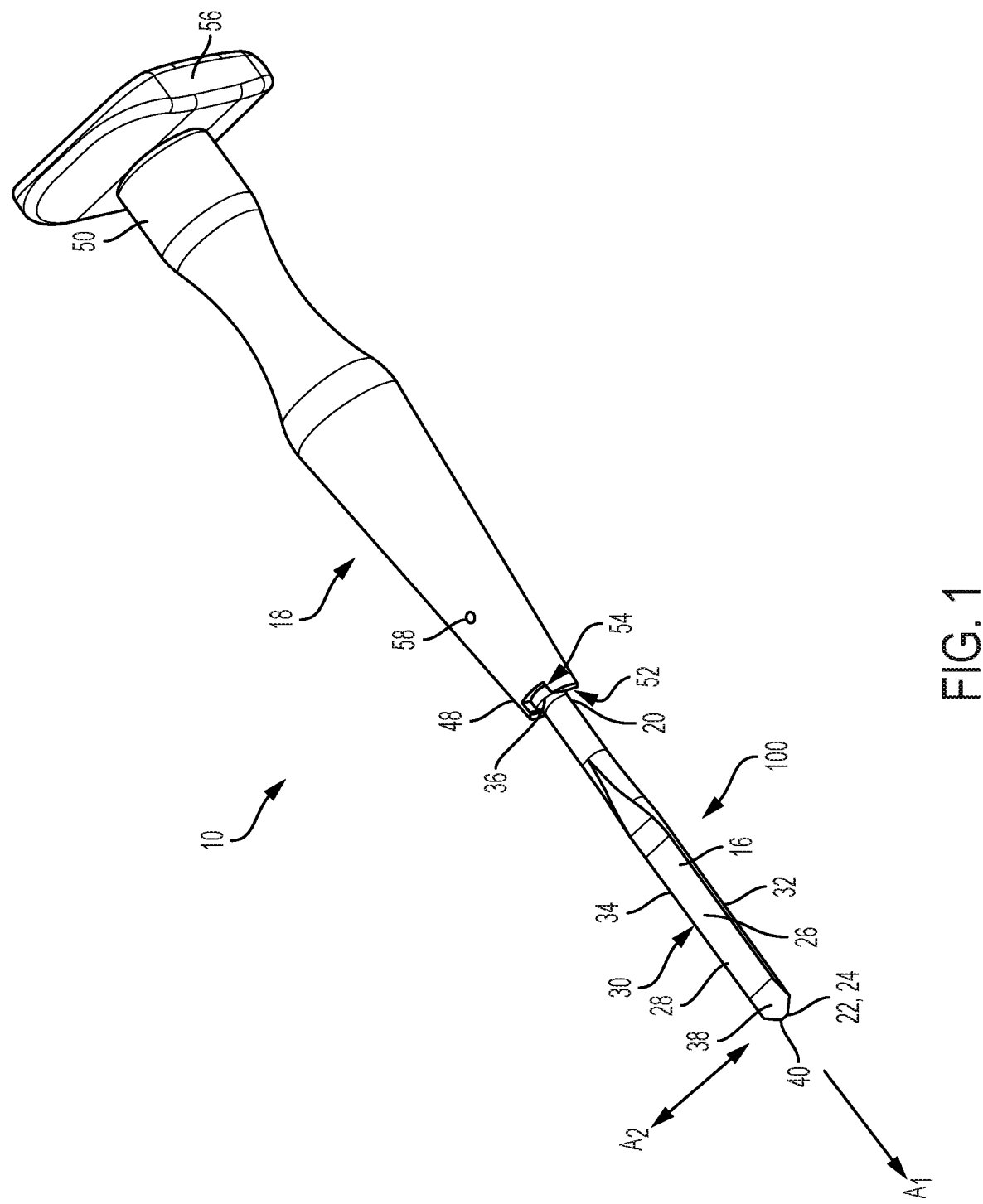
FIG. 1 is a perspective view of the Femoral Hip Stem Explant system of the present application, showing a first blade attached to a handle, according to one aspect.
Figure 2:
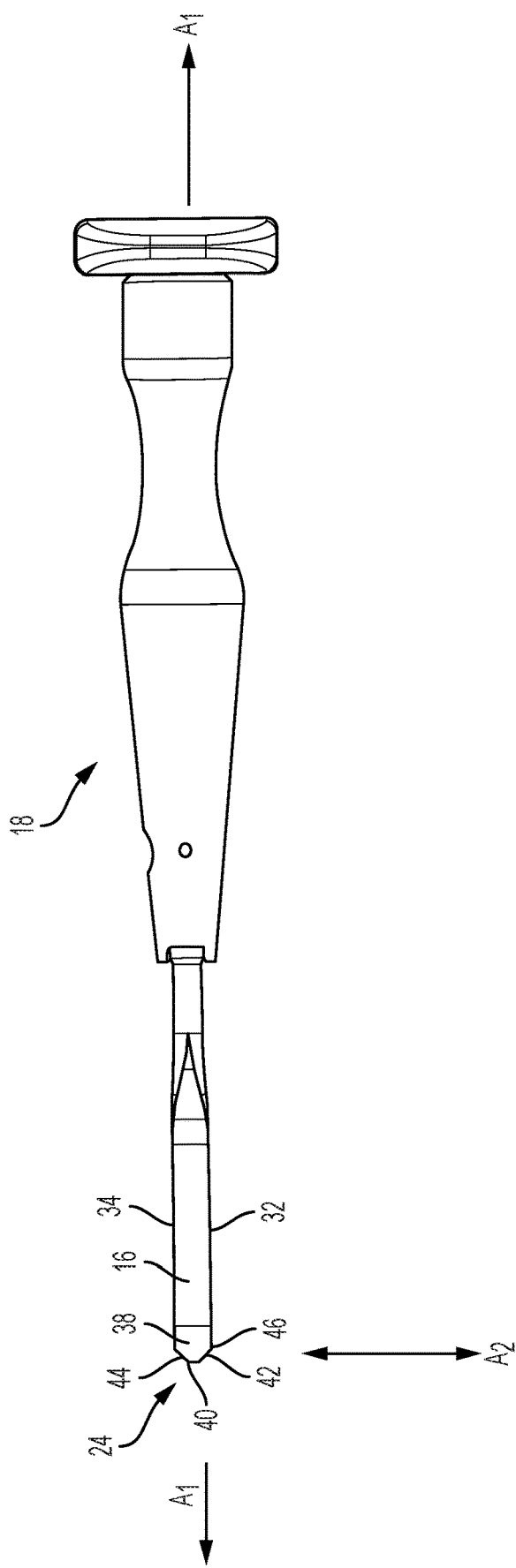
FIG. 2 is a front elevational view of the Femoral Hip Stem Explant system of FIG. 1.
Figure 3:
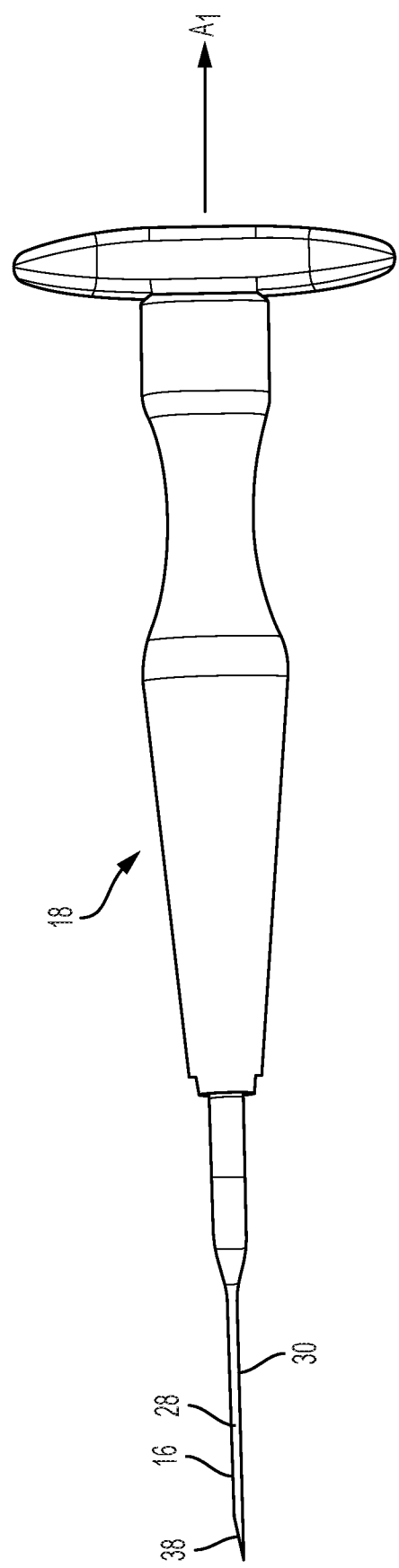
FIG. 3 is a side elevational view of the Femoral Hip Stem Explant system of FIG. 1.
Figure 4:
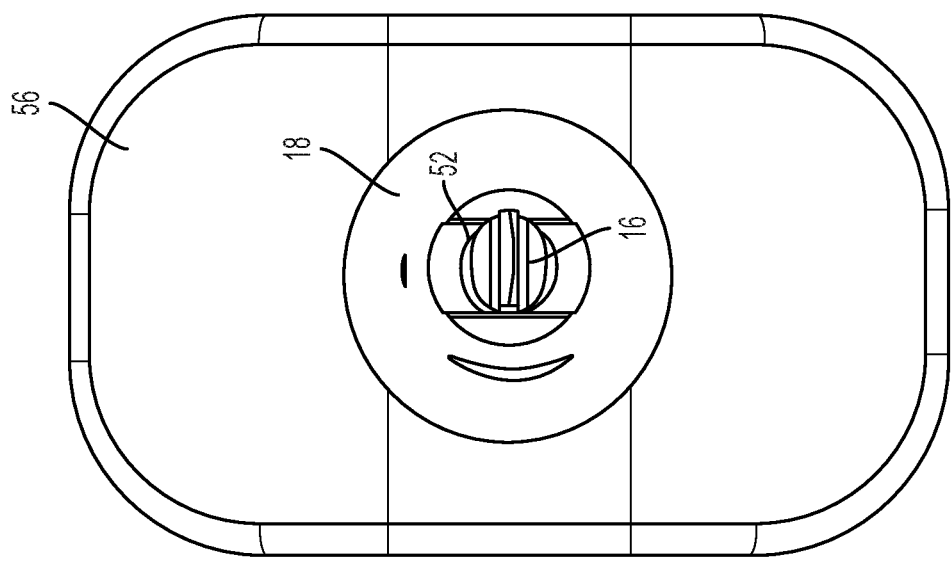
FIG. 4 is a bottom elevational view of the Femoral Hip Stem Explant system of FIG. 1.
Figure 5:
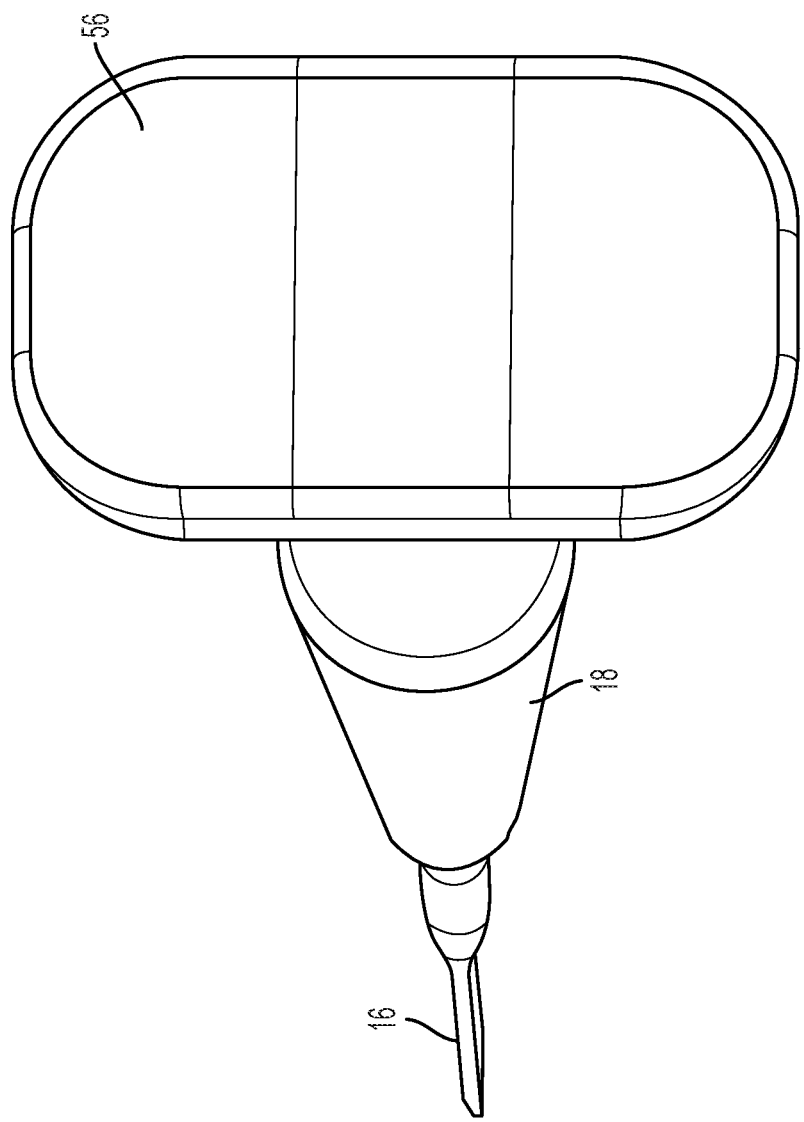
FIG. 5 is a top perspective view of the Femoral Hip Stem Explant system of FIG. 1.
Figure 6:
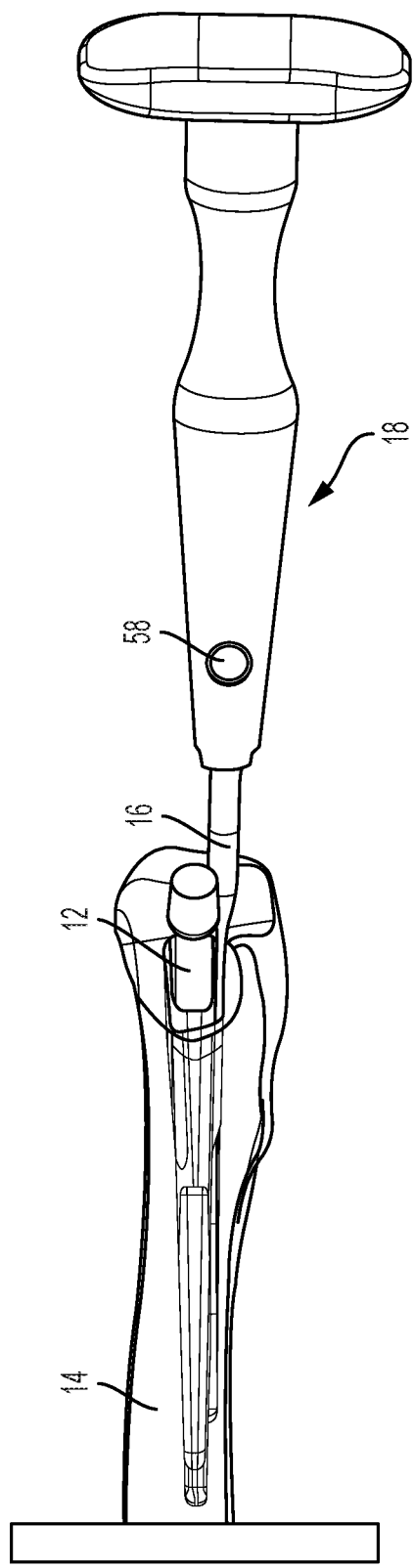
FIG. 6 is a perspective view of the Femoral Hip Stem Explant system of FIG. 1, showing a portion of the blade positioned between a femur and the implant, wherein the femur is shown transparently for clarity.
Figure 7:
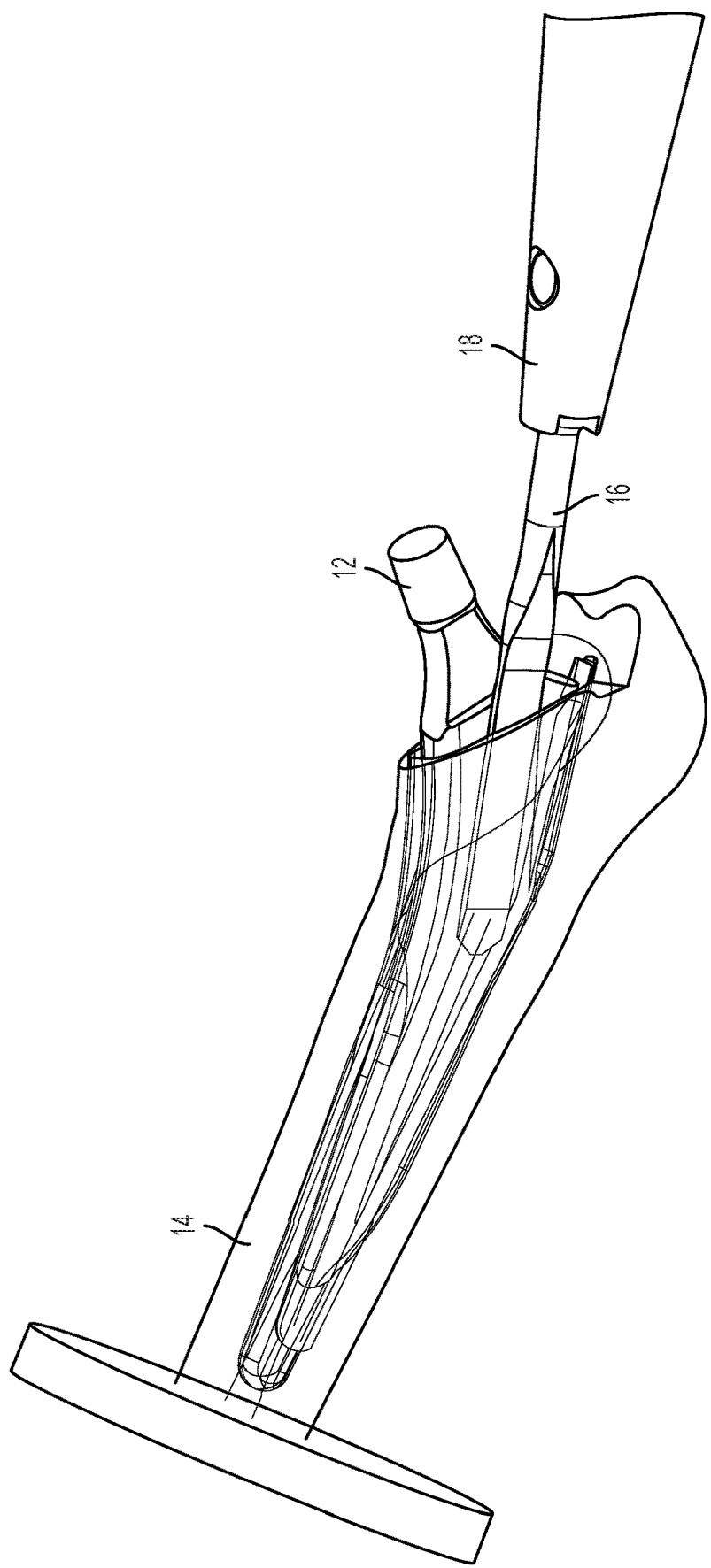
FIG. 7 is a perspective view of the Femoral Hip Stem Explant system of FIG. 1, showing a portion of the blade positioned between a femur and the implant, wherein the femur is shown transparently for clarity.

The present invention can be understood more readily by reference to the following detailed description, examples, and claims, and figures, their previous and following description. In the following description, for purposes of explanation, specific details are set forth in order to provide a thorough understanding of different aspects of the present invention. It will be evident, however, to one skilled in the art that the present invention as defined by the claims may include some or all of the features or embodiments herein described and may further include obvious modifications and equivalents of the features and concepts described herein. It is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting unless included in the claims.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "blade" includes aspects having two or more such blades unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect and "about" is utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

Additionally, as used herein, relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

The application relates generally to a system for the removal of hip implants. More specifically, the present invention relates to a Femoral Hip Stem Explant system 10 that facilitates the removal of a prosthetic implant 12 (shown in FIGS. 6 and 7) from the femur 14 (shown in FIGS. 6 and 7). In one aspect, the explant system comprises at least one blade 16 coupled to a handle 18. In another aspect, the explant system 10 comprises a plurality of blades, wherein each blade is configured to conform to a portion of the implant. For example, the system can comprise a first blade 100 (as illustrated in FIGS. 1-7) configured to conform to a portion of the anterior or posterior portions of the implant, a second blade 200 (as illustrated in FIGS. 8-13) configured to conform to a portion of the lateral portion of the implant, and a third blade 300 (as illustrated in FIGS. 14-19) configured to conform to a portion of the medial portion of the implant. In use, the user can use the handle to guide a blade to a desired position relative to the implant 12.

Referring now to FIGS. 1-7, the first blade 100 has a longitudinal axis $A_1$. In one aspect, the blade comprises a proximal end 20 attachable to the handle 18, an opposed distal end 22 forming a blade tip 24, and a central portion 26 positioned between the proximal end and the distal end. The cutting blade 16 has a first face 28 and an opposed second face 30. The first face and the second face can be formed on a portion of the proximal end 20, the distal end 22 and/or the central portion 26 of the blade. In another aspect, a left edge 32 and an opposed right edge 34 can each extend between the first face 28 and the second face 30 such that the blade has a blade thickness.

The proximal end 20 of the cutting blade 16 can be substantially circular in cross-sectional shape. Optionally, at least one attachment face 36 can be formed in a portion of the proximal end to prevent or restriction rotation of the blade relative to the handle 18. As the blade extends from the proximal end 20 toward the distal end 22, the blade can taper into the first face 28 and the second face 30.

In one aspect, at least a portion of the first face 28 and/or the second face 30 can be planar or substantially planar in a plane that is parallel to the longitudinal axis $A_1$. For example, at least a portion of the first face can be a flat surface that is parallel to a portion of the second face. Alternatively, however, at least a portion of the first face 28 can be a flat surface that is at an acute angle relative to a portion of the second face 30. In another aspect, at least a portion of the left edge 32 and/or the right edge 34 can be planar or substantially planar in a plane that is parallel to the longitudinal axis $A_1$. For example, at least a portion of the left edge can be a flat surface that is parallel to a portion of the right edge. Alternatively, however, at least a portion of the left edge 32 can be a flat surface that is at an acute angle relative to a portion of the right edge 34.

At the distal end 22 of the blade 16, the blade thickness can decrease so that the distance between the first face 28 and the second face 30 becomes smaller such that a cutting edge 38 can be formed at the blade tip 24. That is, according to one aspect, at the distal end of the blade, the first face can taper toward the second face until the cutting edge having a desired blade thickness has been formed at the blade tip. In another aspect, the blade thickness can be substantially constant along the blade tip 24. Alternatively, the blade thickness can vary at different portions of the blade tip. For example, the blade thickness can be greater at the left edge 32 and/or the right edge 34 than a central element 40 of the blade tip 24. In another example, the blade thickness can be smaller at the left edge and/or the right edge than the central element of the blade tip.

In one aspect, the blade tip 24 can have a blade axis $A_2$ that is normal or substantially normal to the longitudinal axis $A_1$ of the blade 16. For example, the blade tip can be a linear tip extending along the blade axis $A_2$. Optionally, a portion of the blade tip can be beveled. For example, at least a portion of the blade tip 24 can be at an acute angle relative to the blade axis. In one aspect, the blade tip can have the central element 40 positioned along the blade axis A2, a first element 42 beveled towards the left edge 32 and a second element 44 beveled towards the right edge 34. Thus, the central element can be a predetermined distance from the handle 18 that is greater than the distance from the handle to a distal end 46 of the left edge.

Referring now to FIGS. 8-13, the second blade 200 has a longitudinal axis $A_1$. In one aspect, the cutting blade 216 comprises the proximal end 220 attachable to the handle 18, the opposed distal end 222 forming the blade tip 224, and the central portion 226 positioned between the proximal end and the distal end. The cutting blade 216 has the first face 228 and the opposed second face 230. The first face and the second face can be formed on a portion of the proximal end 220, the distal end 222 and/or the central portion 226 of the blade. In another aspect, the left edge 232 and the opposed right edge 234 can each extend between the first face 228 and the second face 230 such that the blade has a blade thickness.

The proximal end 220 of the cutting blade 216 can be substantially circular in cross-sectional shape. As the blade extends from the proximal end 220 toward the distal end 222, the blade can taper into the first face 228 and the second face 230. In one aspect, at least a portion of the first face 228 and/or the second face 230 can be arcuate in shape and can extend in a direction that is substantially parallel to the longitudinal axis $A_1$. For example, at least a portion of the first face can be a curved face that is parallel to a portion of the second face. Alternatively, however, at least a portion of the first face 228 can be a curved surface that is not parallel to a portion of the second face 230. In another aspect, the first face and/or the second face can have a substantially constant radius. Alternatively, the radius of the first face 228 and/or the second face 230 can vary at different portions relative to the proximal end 220 of the blade 216.

Figure 9:
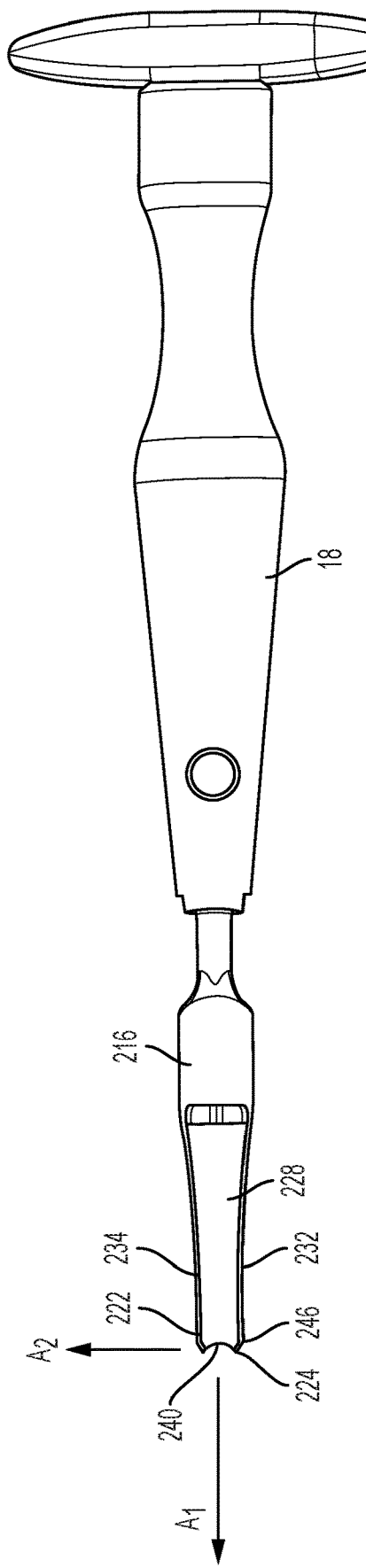
FIG. 9 is a front elevational view of the Femoral Hip Stem Explant system of FIG. 8.
Figure 10:
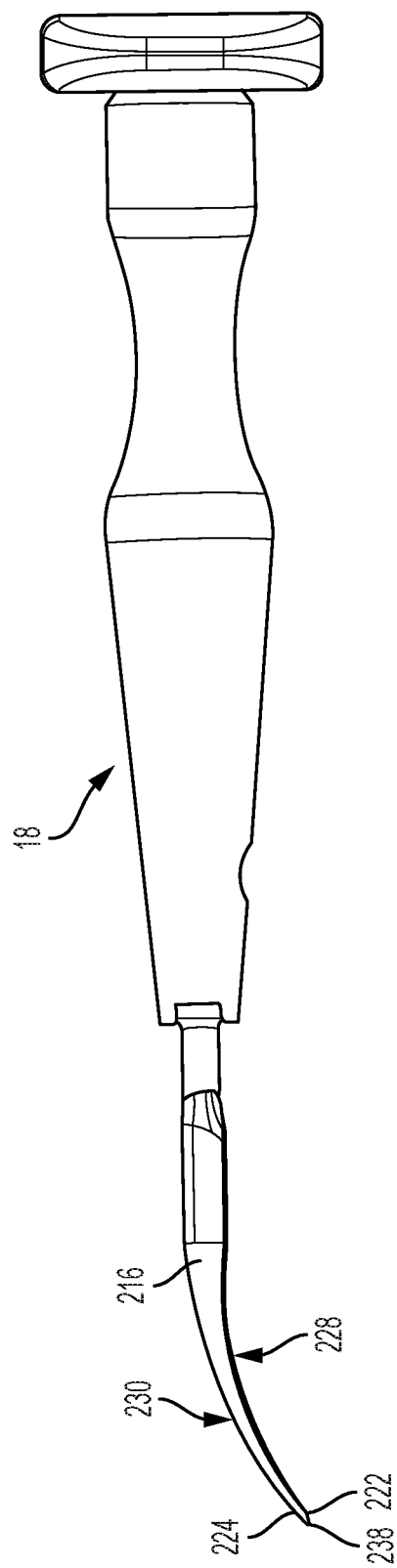
FIG. 10 is a side elevational view of the Femoral Hip Stem Explant system of FIG. 8.
Figure 11:
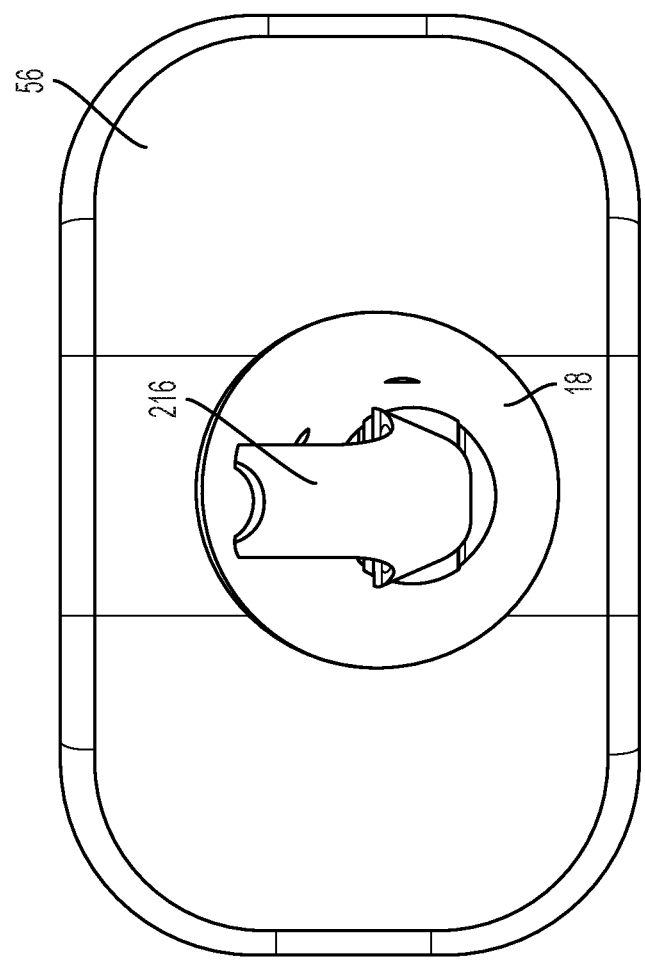
FIG. 11 is a bottom elevational view of the Femoral Hip Stem Explant system of FIG. 8.
Figure 12:
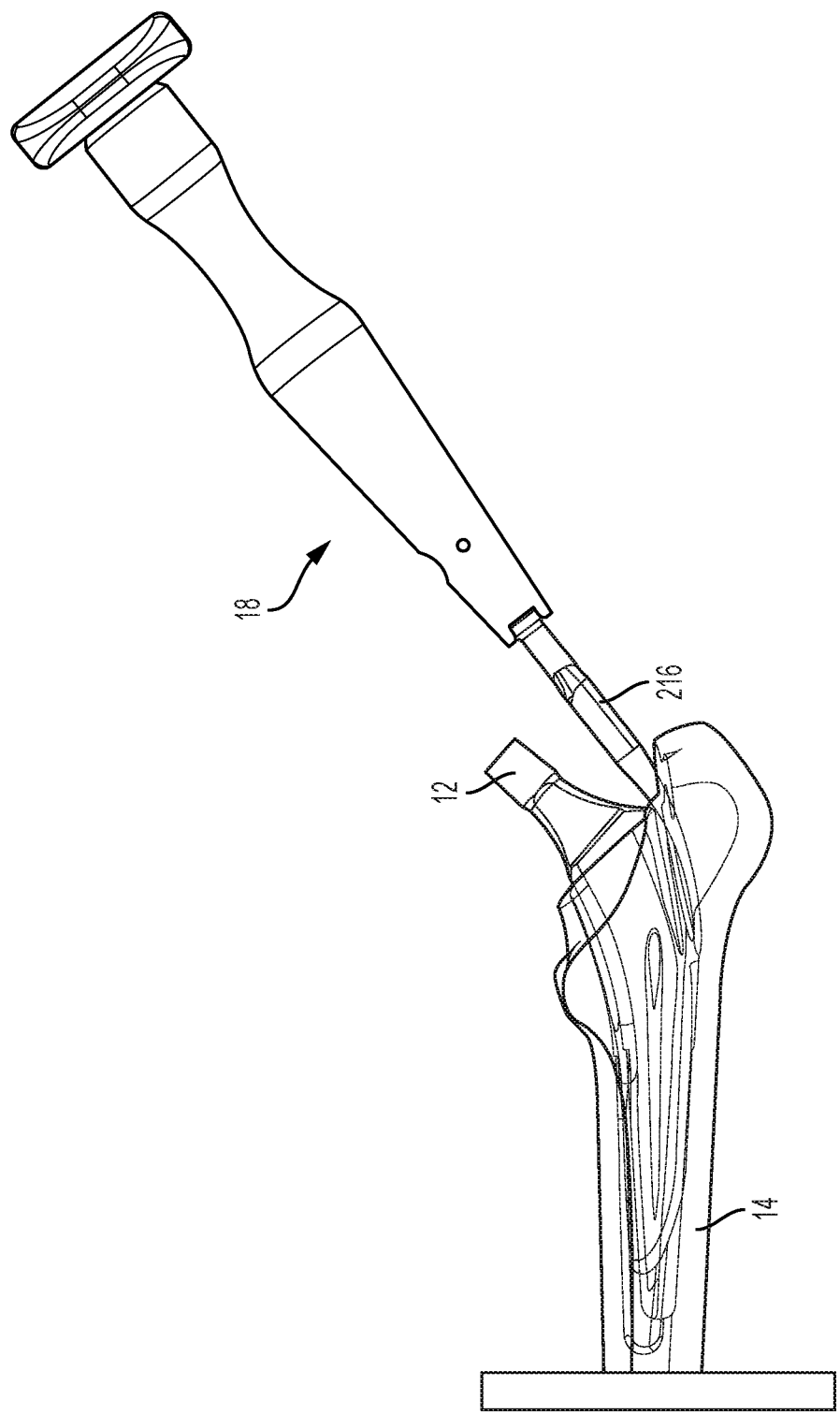
FIG. 12 is a perspective view of the Femoral Hip Stem Explant system of FIG. 8, showing a portion of the blade positioned between a femur and the implant, wherein the femur is shown transparently for clarity.
Figure 13:
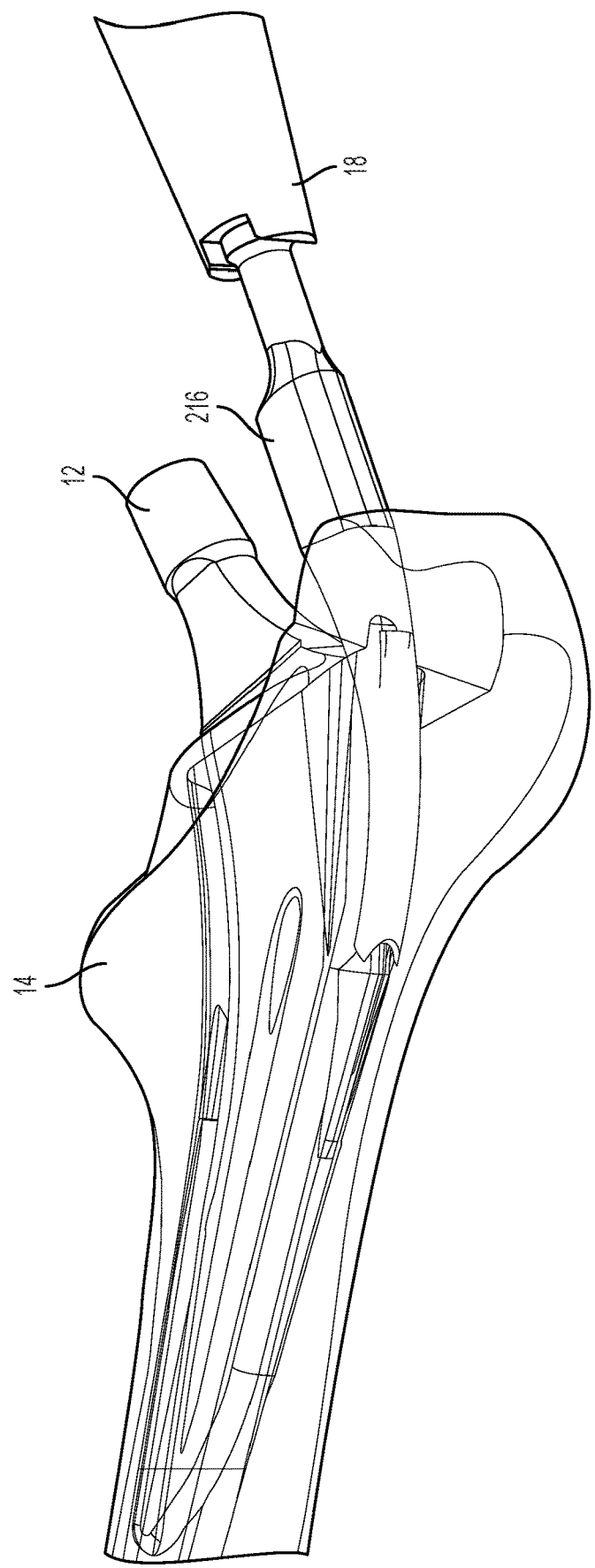
FIG. 13 is a perspective view of the Femoral Hip Stem Explant system of FIG. 8, showing a portion of the blade positioned between a femur and the implant, wherein the femur is shown transparently for clarity.

In another aspect, at least a portion of the left edge 232 and/or the right edge 234 can be substantially planar in a plane that is parallel to the longitudinal axis $A_1$. For example, at least a portion of the left edge can be parallel to a portion of the right edge when viewed from the front, as illustrated in FIG. 9. Alternatively, however, at least a portion of the left edge 232 and/or the right edge 234 can be at an acute angle relative to the longitudinal axis $A_1$. In yet another aspect, at least a portion of the left edge and/or the right edge can be arcuate in shape. For example, the width of the blade 216 can decrease as the blade tip 224 nears, and the arcuate shape of the left edge 232 and/or right edge 234 can lead to this narrower width. In another aspect, the left edge and/or the right edge can have a substantially constant radius. Alternatively, the radius of the left edge 232 and/or the right edge 234 can vary at different portions relative to the proximal end 220 of the blade 216.

Figure 8:
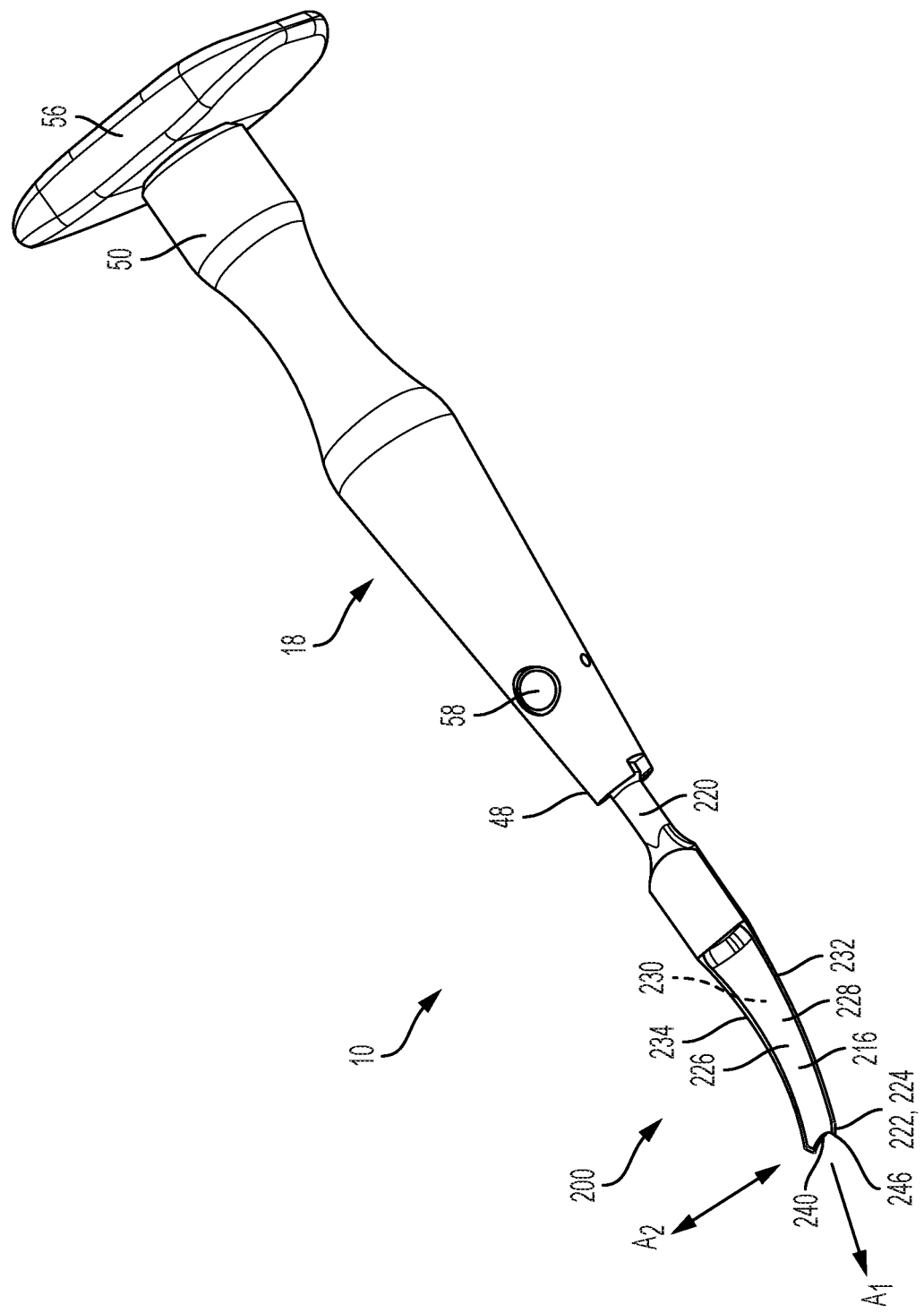
FIG. 8 is a perspective view of the Femoral Hip Stem Explant system of the present application, showing a second blade attached to a handle, according to another aspect.

At the distal end 222 of the blade 216, the blade thickness can decrease so that the distance between the first face 228 and the second face 230 becomes smaller such that the cutting edge 238 can be formed at the blade tip 224. That is, according to one aspect, at the distal end of the blade, the first face can taper toward the second face until the cutting edge having a desired blade thickness has been formed at the blade tip. In another aspect, the blade thickness can be substantially constant along the blade tip 224. Alternatively, and as illustrated in FIG. 8, the blade thickness can vary at different portions of the blade tip. For example, the blade thickness can be greater at the left edge 232 and/or the right edge 234 than at the central element 240 of the blade tip 224. In another example, the blade thickness can be smaller at the left edge 232 and/or the right edge 234 than at the central element of the blade tip.

In another aspect, the blade tip 224 can have a blade axis $A_2$ that is substantially normal to the longitudinal axis $A_1$ of the blade 216. For example, the blade tip can be a linear tip extending along the blade axis $A_2$. Optionally, at least a portion of the blade tip 224 can be arcuate in shape. For example, the distance from the blade tip 224 at the distal edge 246 of the left edge 232 to the proximal end 220 of the blade 216 can be greater than the distance from the central element 240 of the blade tip to the proximal end of the blade. In another aspect, the blade tip can have a substantially constant radius. Alternatively, the radius of the blade tip 224 can vary at different portions relative to the left edge 232 of the blade 216.

Referring now to FIGS. 14-19, the third blade 300 has a longitudinal axis $A_1$. In one aspect, the cutting blade 316 comprises the proximal end 320 attachable to the handle 18, the opposed distal end 322 forming the blade tip 324, and the central portion 326 positioned between the proximal end and the distal end. The cutting blade 316 has the first face 328 and the opposed second face 330. The first face and the second face can be formed on a portion of the proximal end 320, the distal end 322 and/or the central portion 326 of the blade. In another aspect, the left edge 332 and the opposed right edge 334 can each extend between the first face 328 and the second face 330 such that the blade has a blade thickness.

The proximal end 320 of the cutting blade 316 can be substantially circular in cross-sectional shape. As the blade extends from the proximal end 320 toward the distal end 322, the blade can taper into the first face 328 and the second face 330. In one aspect, at least a portion of the first face 328 and/or the second face 330 can be arcuate in shape and can extend in a direction that is substantially parallel to the longitudinal axis $A_1$. For example, at least a portion of the first face can be a curved face that is parallel to a portion of the second face. Alternatively, however, at least a portion of the first face 328 can be a curved surface that is not parallel to a portion of the second face 330. In another aspect, the first face and/or the second face can have a substantially constant radius. Alternatively, the radius of the first face 328 and/or the second face 330 can vary at different portions relative to the proximal end 320 of the blade 316.

Figure 15:
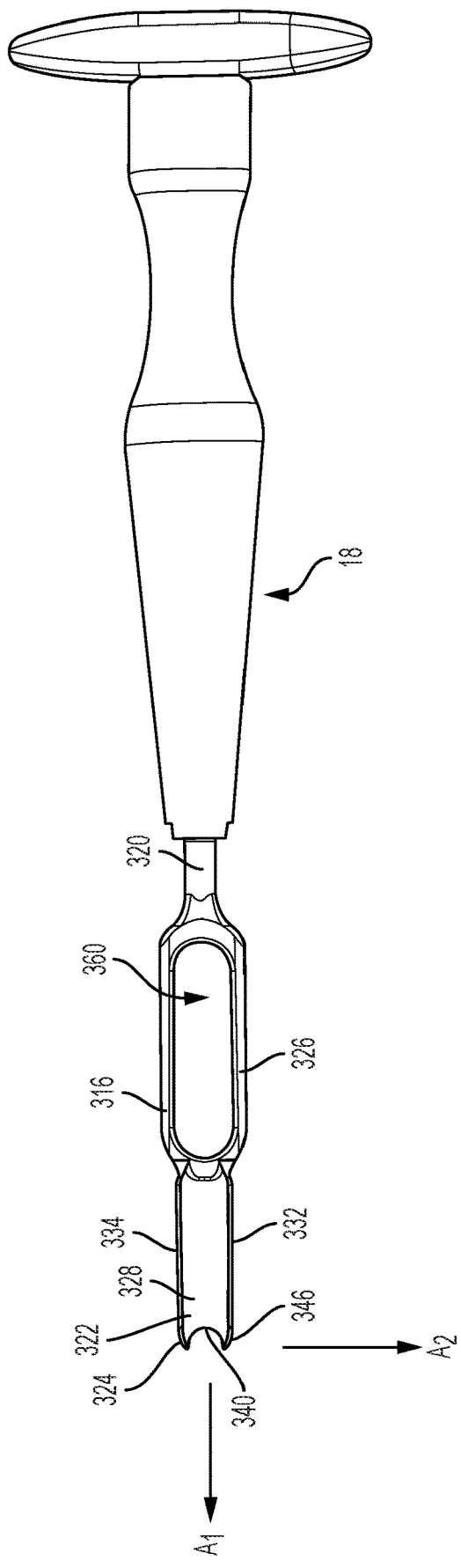
FIG. 15 is a front elevational view of the Femoral Hip Stem Explant system of FIG. 14.
Figure 16:
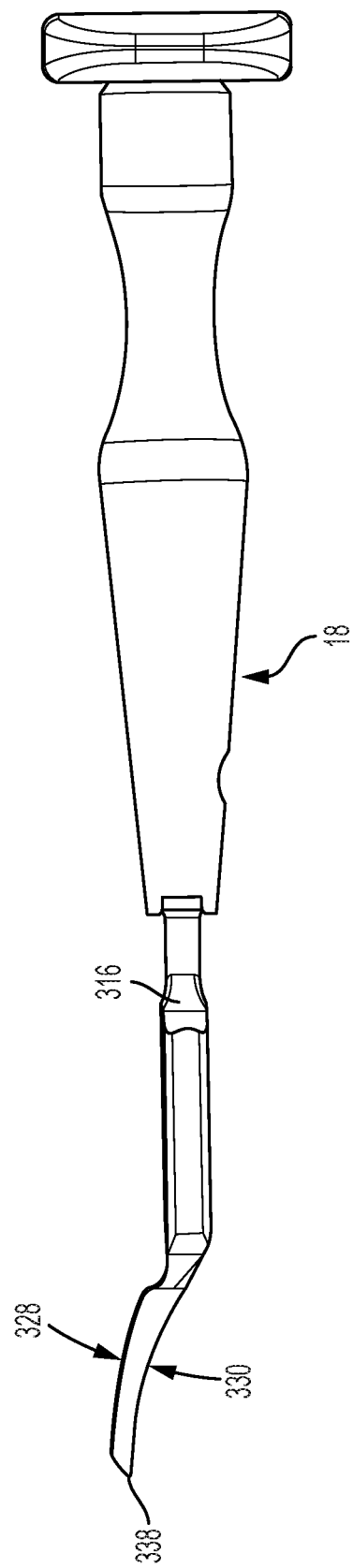
FIG. 16 is a side elevational view of the Femoral Hip Stem Explant system of FIG. 14.
Figure 17:
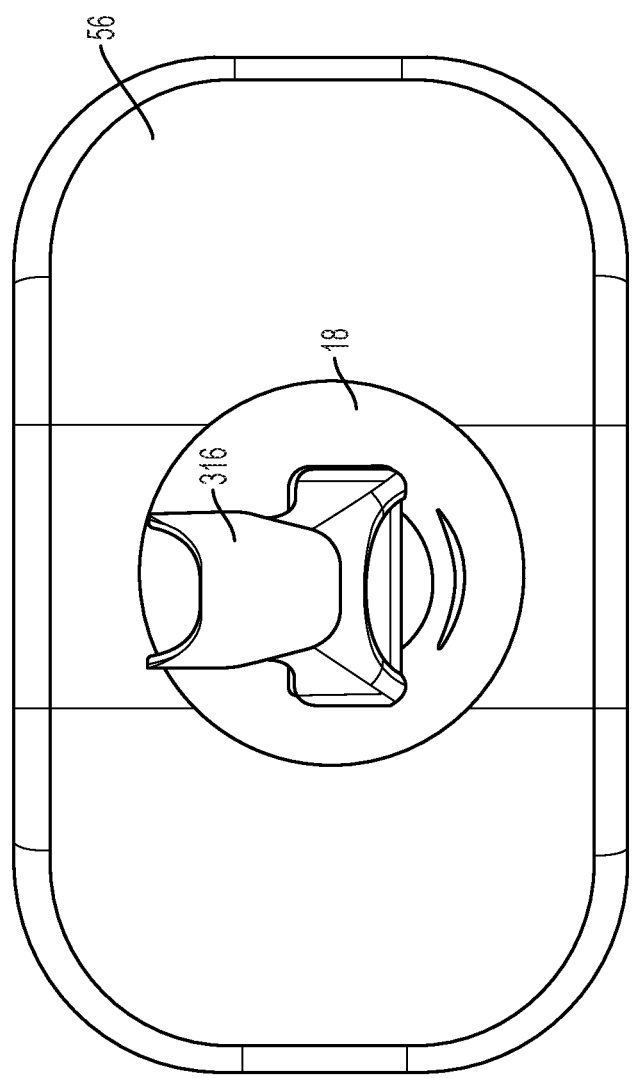
FIG. 17 is a bottom elevational view of the Femoral Hip Stem Explant system of FIG. 14.
Figure 18:
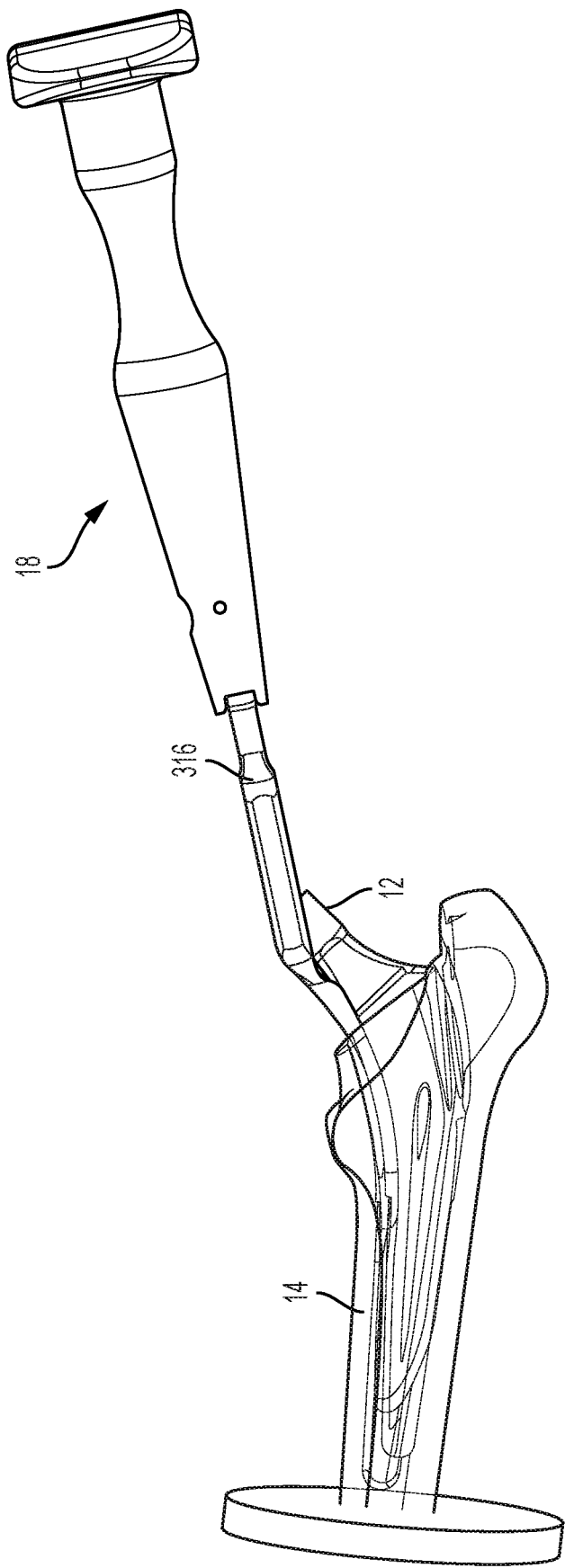
FIG. 18 is a perspective view of the Femoral Hip Stem Explant system of FIG. 14, showing a portion of the blade positioned between a femur and the implant, wherein the femur is shown transparently for clarity.
Figure 19:
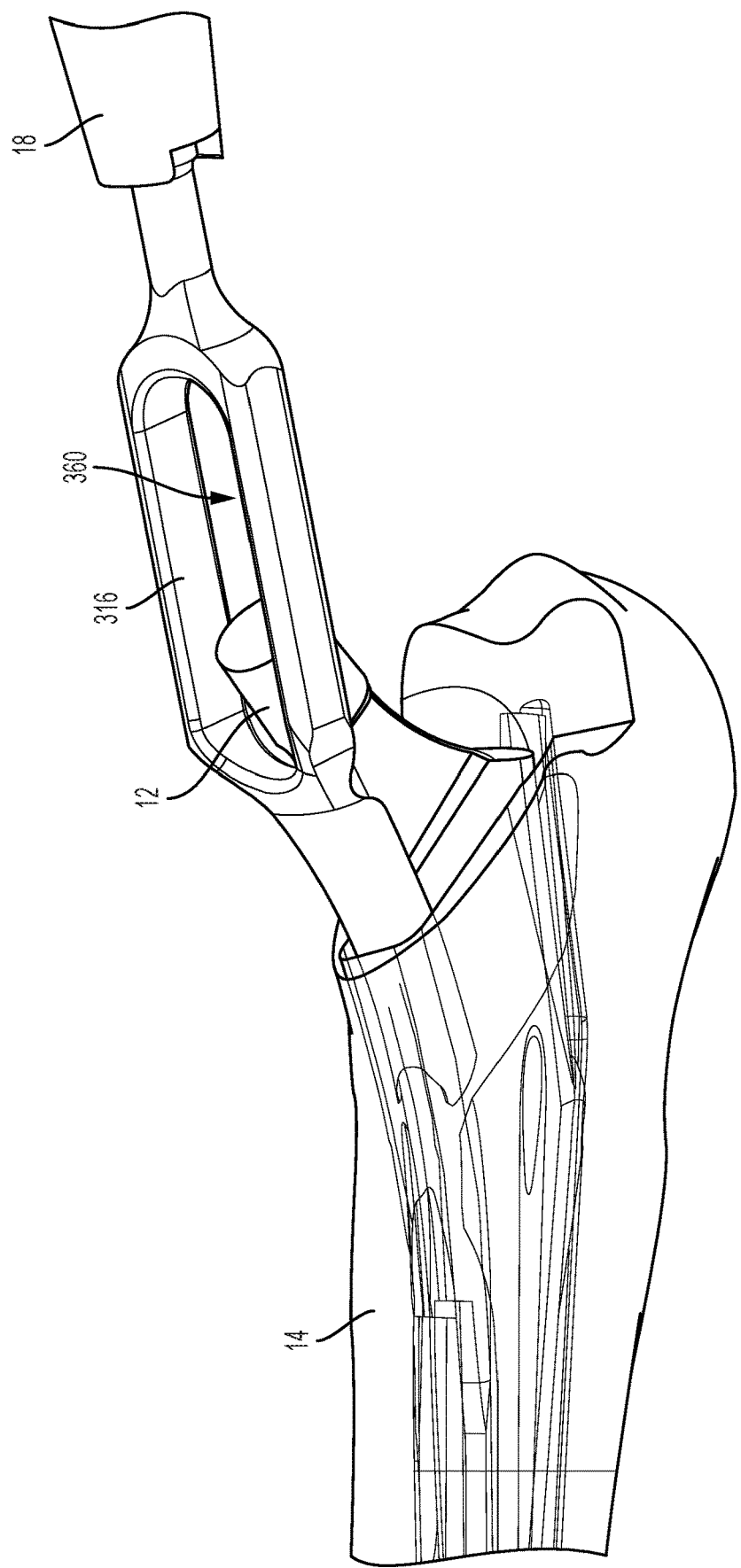
FIG. 19 is a perspective view of the Femoral Hip Stem Explant system of FIG. 14, showing a portion of the blade positioned between a femur and the implant, wherein the femur is shown transparently for clarity.

In another aspect, at least a portion of the left edge 332 and/or the right edge 334 can be substantially planar in a plane that is parallel to the longitudinal axis $A_1$. For example, at least a portion of the left edge can be parallel to a portion of the right edge when viewed from the front, as illustrated in FIG. 15. Alternatively, however, at least a portion of the left edge 332 and/or the right edge can be at an acute angle relative to the longitudinal axis $A_1$. In yet another aspect, at least a portion of the left edge and/or the right edge 334 can be arcuate in shape. For example, the width of the blade 316 can decrease as the blade tip 324 nears, and the arcuate shape of the left edge 332 and/or right edge can lead to this narrower width. In another aspect, the left edge and/or the right 334 edge can have a substantially constant radius. Alternatively, the radius of the left edge 332 and/or the right edge can vary at different portions relative to the proximal end 320 of the blade 316.

Figure 14:
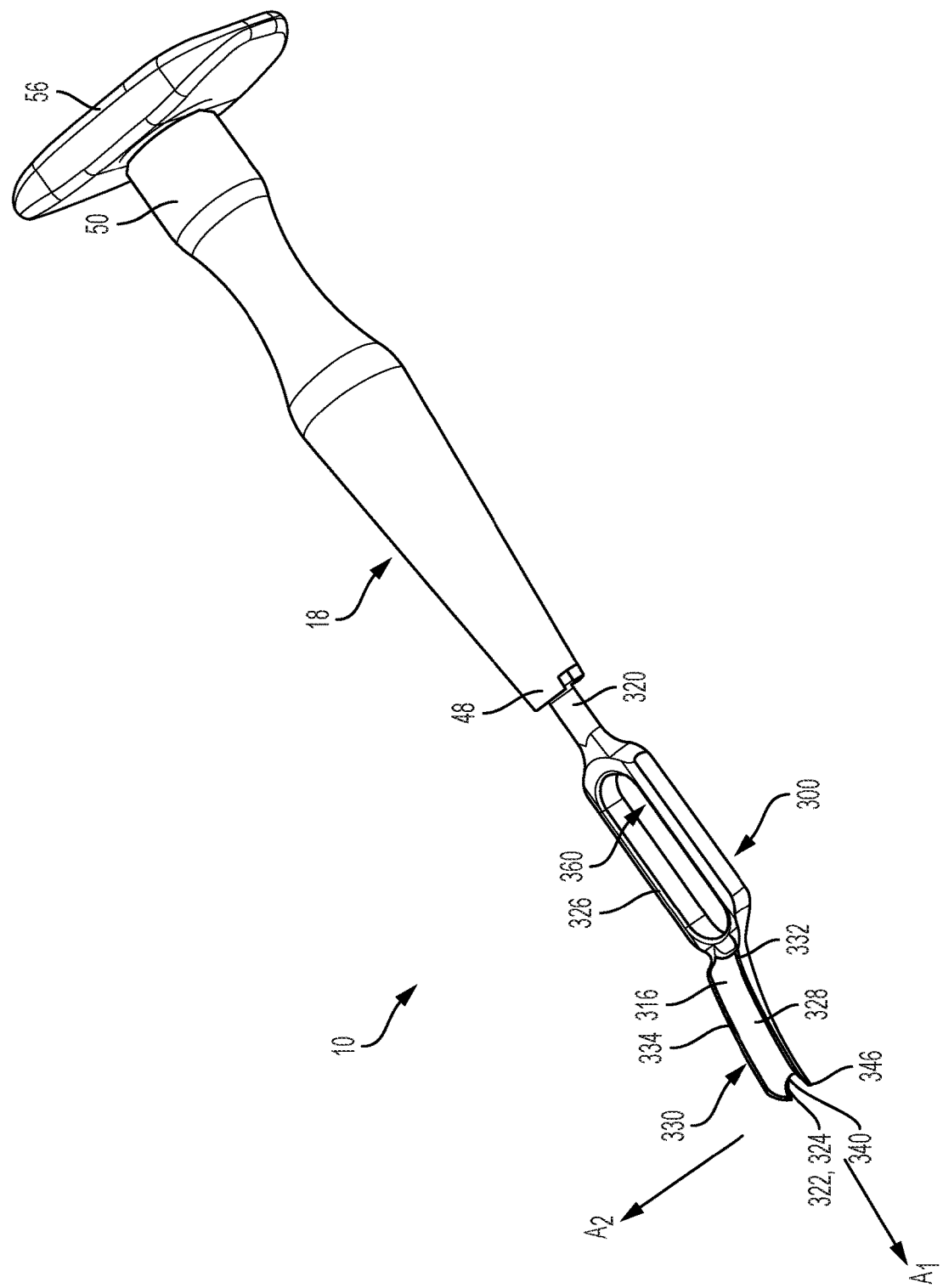
FIG. 14 is a perspective view of the Femoral Hip Stem Explant system of the present application, showing a third blade attached to a handle, according to another aspect.

At the distal end 322 of the blade 316, the blade thickness can decrease so that the distance between the first face 328 and the second face 330 becomes smaller such that the cutting edge 338 can be formed at the blade tip 324. That is, according to one aspect, at the distal end of the blade, the first face can taper toward the second face until the cutting edge having a desired blade thickness has been formed at the blade tip. In another aspect, the blade thickness can be substantially constant along the blade tip 324. Alternatively, and as illustrated in FIG. 14, the blade thickness can vary at different portions of the blade tip. For example, the blade thickness can be greater at the left edge 332 and/or the right edge 334 than at the central element 340 of the blade tip 324. In another example, the blade thickness can be smaller at the left edge 332 and/or the right edge 334 than at the central element of the blade tip.

In another aspect, the blade tip 324 can have a blade axis $A_2$ that is substantially normal to the longitudinal axis $A_1$ of the blade 316. For example, the blade tip can be a linear tip extending along the blade axis $A_2$. Optionally, at least a portion of the blade tip 324 can be arcuate in shape. For example, the distance from the blade tip 324 at the distal edge 346 of the left edge 332 to the handle 18 can be greater than the distance from the central element 340 of the blade tip to the handle. In another aspect, the blade tip can have a substantially constant radius. Alternatively, the radius of the blade tip 324 can vary at different portions relative to the left edge 332 of the blade 316.

In one aspect, the central portion of the blade 316 can have a blade width that is greater than the blade width of the proximal end 320 and the distal end 322 of the blade. In another aspect, a slot 360 or other void or opening can be defined in the central portion 326 of the blade. For example, the slot can be a longitudinal slot extending along the longitudinal axis $A_1$ of the blade 316. In this aspect, the slot 360 can be sized and shaped to conform to a portion of the implant 12. That is, the slot can be sized and shaped such that a portion of the implant can extend through the slot 360 so that the blade tip 324 can access a desired position relative to the implant 12. Thus, the slot can be sized and shaped so that the central portion 326 of the blade does not undesirably engage the implant, thereby restricting access of the blade tip to a desired position.

The handle 18 can be attachable to the blade 16 and configured to allow the user to guide the blade tip 24 to a desired position. In one aspect, the handle can have a distal end 48 and an opposed proximal end 50. A bore 52 can be defined in a portion of the distal end of the handle. In another aspect, the bore can be sized and shaped to matingly engage the proximal end 20 of the blade. For example, an attachment face 54 can be formed in an outer wall of the bore such that the attachment face of the bore 52 can matingly engage the attachment face 36 of the blade 16 to prevent or restriction rotation of the blade relative to the handle 18. A strikeplate 56 can be positioned at the proximal end of the handle to provide the user a solid surface with which to urge the blade 16 to the desired position.

In one aspect, the blade 16 can be securely, permanently attached to the handle 18. Optionally, in other aspects, the blade can be selectively detachable from the handle. For example, a releasable locking mechanism 58 can releasably secure the blade 16 to the handle 18.

The blade 16 and/or the handle 18 can be made from biocompatible materials, such as, for example and without limitation, stainless steel or titanium. The blade and/or the handle can be anodized and re-sterilizable. In one aspect, the blade 16 and/or the handle 18 can be provided in a range of sizes as necessary to conform to different sized implants 12. Preferably, blade 16 is not flexible but is instead rigid. Preferably, blade 16 does not bend to the shape of the implant during use but is instead pre-contoured to conform to the geometry of the relevant portion of the implant and configured to cut through femur growing into the lateral portion of the implant. Preferably, blade 16 is adapted to remain rigid enough to deliver the impact force to the stem/bone interface or stem/cement interface. Preferably, blade 16 is made of high strength Stainless steel. According to preferred embodiments, blade 16 is made of a material (e.g., stainless steel, titanium) having a tensile strength (ultimate) greater than 1100 MPa, and preferably with a hardness value of $R_c$ 33-45.

To assemble the Femoral Hip Stem Explant system 10, the proximal end 20 of the at least one blade 16 can be inserted into the bore 52 of the handle 18 to secure the blade to the handle. If the at least one blade comprises a plurality of blades, such as the first blade 100, the second blade 200, or the third blade 300, the desired blade of the plurality of blades 16 can be inserted into the bore of the handle to secure the blade to the handle 18.

In use, the Femoral Hip Stem Explant system 10 can be used to aid in the removal of a well-fixed hip stem implant 12 during hip revision surgeries. In one aspect, the blade tip 24 can be positioned adjacent to a portion of the implant such that the cutting edge 38 is between the implant and the femur 14. The user can apply force to the strikeplate 56 which urges the sharp cutting edge to cut through portions of the femur growing into the implant 12. The user can then move the blade 16 to a different location relative to the implant and the femur 14 and repeat the process. As the user moves to different portions of the implant 12, a different blade can be used to conform to the geometry of that portion of the implant. For example, if the user desires to remove bone growth into and adjacent to the anterior or posterior portions of the implant 12, the first blade 100 of FIGS. 1-7 can be used. In another example, if the user desires to remove bone growth into and adjacent to the lateral portion of the implant, the second blade 200 of FIGS. 8-13 can be used. In still another example, if the user desires to remove bone growth into and adjacent to the medial portion of the implant 12, the third blade 300 of FIGS. 14-19 can be used. As can be appreciated, the blades can be coupled to different handles 18, or optionally, the blades can be interchanged with a single handle.

The scope of the present devices, systems and methods, etc., includes both means plus function and step plus function concepts. However, the claims are not to be interpreted as indicating a "means plus function" relationship unless the word "means" Is specifically recited in a claim, and are to be interpreted as indicating a "means plus function" relationship where the word "means" is specifically recited in a claim. Similarly, the claims are not to be interpreted as indicating a "step plus function" relationship unless the word "step" is specifically recited in a claim, and are to be interpreted as indicating a "step plus function" relationship where the word "step" is specifically recited in a claim.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A medial blade for removing a hip implant from a femur, the medial blade comprising a medial cutting blade having a proximal end and a distal end and wherein the medial cutting blade conforms to the geometry of the medial portion of the hip implant and is configured to cut through femur growing into the medial portion of the hip implant and further comprises a slot opening defined through a central portion of the medial blade between the proximal end of the medial blade and the distal end of the medial blade and wherein the slot opening is sized and shaped such that a portion of the hip implant can pass through the slot opening so that the medial blade does not undesirably engage the hip implant restricting access of the medial cutting blade when removing the hip implant.

2. The medial blade of claim 1, wherein the slot opening is sized and shaped to conform to at least a portion of the hip implant.

3. The medial blade of claim 1, wherein the slot opening is a longitudinal slot opening extending along the longitudinal axis of the medial blade.

4. The medial blade of claim 1, wherein the distal end of the medial cutting blade has a first face and opposed second face and the first face and the opposed second face are arcuate in shape.

5. The medial blade of claim 1, wherein the distal end comprises a blade tip having an arcuate shape.

6. The medial blade of claim 1, wherein the medial blade has a proximal end and a distal end and wherein the central portion of the medial blade has a blade width greater than the blade width of the proximal end of the medial blade and greater than the blade width of the distal end of the medial blade.

7. A method of removing a hip implant from a femur using the medial blade of claim 1, the method comprising cutting through femur growing into the medial portion of the hip implant using the medial blade thereby facilitating removal of the hip implant.

8. A system for removing a hip implant from a femur, the system comprising:
(a) a first blade having a proximal end and a distal end and the first blade further comprising a cutting blade having a proximal end and a distal end; and
(b) a handle,
wherein the first blade is attachable to the handle and wherein the distal end of the cutting blade includes a cutting tip configured to cut through bone growth from the femur into the hip implant thereby facilitating removal of the hip implant and wherein the cutting blade is configured to conform to the geometry of a portion of the hip implant and wherein the first blade comprises an elongated slot opening defined in the first blade between the proximal end of the first blade and the distal end of the first blade and wherein the elongated slot opening is defined in a central portion of the first blade and the central portion has a blade width greater than the blade width of the proximal end of the first blade and greater than the blade width of the distal end of the first blade.

9. The system of claim 8, further comprising a lateral blade having a proximal end and comprising a lateral cutting blade having a proximal end and a distal end and wherein the lateral cutting blade is configured to conform to the geometry of the lateral portion of the hip implant and is configured to cut through femur growing into the lateral portion of the hip implant.

10. The system of claim 8, wherein the first blade is a medial blade having a proximal end and comprising a medial cutting blade having a proximal end and a distal end and wherein the medial cutting blade is configured to conform to the geometry of the medial portion of the hip implant and is configured to cut through femur growing into the medial portion of the hip implant.

11. The system of claim 8, wherein the elongated slot opening is defined in a central portion of the first blade between the proximal end of the first blade and the distal end of the first blade and is sized and shaped to conform to at least a portion of the hip implant.

12. The system of claim 8, wherein the elongated slot opening is a longitudinal elongated slot opening extending along the longitudinal axis of the first blade.

13. The system of claim 8, wherein the handle includes a bore for insertion of the proximal end of the first blade.

14. The system of claim 13, wherein the bore comprises an attachment face adapted to matingly engage the proximal end of the first blade and restrict rotation of the first blade relative to the handle.

15. The system of claim 8, wherein the handle comprises a releasable lock to releasably secure the first blade to the handle.

16. The system of claim 8, further comprising a lateral blade and wherein the first blade and the lateral blade are each adapted to be interchanged and used with the handle.

17. The system of claim 8, wherein the elongated slot opening is sized and shaped to conform to at least a portion of the hip implant.

18. A method of removing a hip implant from a femur using the system of claim 8, the method comprising cutting through femur growing into portions of the hip implant using the first blade thereby facilitating removal of the hip implant.

19. A system for removing a hip implant from a femur, the system comprising:
(a) a first blade having a proximal end and a distal end and the first blade further comprising a cutting blade having a proximal end and a distal end; and
(b) a handle,
wherein the first blade is attachable to the handle and wherein the distal end of the cutting blade includes a cutting tip configured to cut through bone growth from the femur into the hip implant or through bone cement surrounding the hip implant, thereby facilitating removal of the hip implant and wherein the cutting blade is configured to conform to the geometry of a portion of the hip implant and wherein the first blade comprises an elongated slot opening defined between the proximal end of the first blade and the distal end of the first blade and wherein the elongated slot opening is sized and shaped such that a portion of the hip implant can pass through the slot opening so that the first blade does not undesirably engage the hip implant restricting access of the cutting blade when removing the hip implant.

20. The system of claim 19, wherein said first blade is permanently attached to the handle.

21. The system of claim 19, wherein the first blade is a medial blade having a proximal end and comprising a medial cutting blade having a proximal end and a distal end and wherein the medial cutting blade is configured to conform to the geometry of at least a medial portion of the hip implant and is configured to cut through femur growing into the medial portion of the hip implant.

22. The system of claim 19, wherein the elongated slot opening is sized and shaped to conform to at least a portion of the hip implant and the elongated slot opening is defined in a central portion of the first blade between the proximal end of the first blade and the distal end of the first blade.

23. The system of claim 19, wherein the elongated slot opening is a longitudinal elongated slot opening extending along the longitudinal axis of the first blade.

24. The system of claim 19, wherein the elongated slot opening is defined in a central portion of the first blade and the central portion has a blade width greater than the blade width of the proximal end of the first blade and greater than the blade width of the distal end of the first blade.

25. A method of removing a hip implant from a femur using the system of claim 19, the method comprising cutting through femur growing into portions of the hip implant using the first blade thereby facilitating removal of the hip implant.

* * * * *

UNITED STATES PATENT AND TRADEMARK OFFICE
CERTIFICATE OF CORRECTION

| | |
|---|---|
| PATENT NO. | : 10,751,070 B2 |
| APPLICATION NO. | : 15/877319 |
| DATED | : August 25, 2020 |
| INVENTOR(S) | : John E. Pendleton, Daniel H. Hursh and Thomas L. Bradbury |

It is certified that error appears in the above-identified patent and that said Letters Patent is hereby corrected as shown below:

On the Title Page

In Column 1, (73) Assignee: replace SHENZHEN RIDER THINKING TECHNOLOGIES CO., LTD., Shenzhen (CN) with -- TIGHTLINE DEVELOPMENT, LLC., Georgia (US) --.

Signed and Sealed this
Twenty-eighth Day of February, 2023

Katherine Kelly Vidal
*Director of the United States Patent and Trademark Office*